United States Patent
Gu et al.

(10) Patent No.: US 9,301,694 B2
(45) Date of Patent: *Apr. 5, 2016

(54) OPTICAL FINGER MOUSE, ELECTRONIC DEVICE AND PHYSIOLOGICAL CHARACTERISTICS DETECTION DEVICE

(75) Inventors: Ren Hau Gu, Hsin-Chu (TW); Ming Tsan Kao, Hsin-Chu (TW); Sen Huang Huang, Hsin-Chu (TW)

(73) Assignee: PIXART IMAGING INC., Hsin-Chu County (TW)

( * ) Notice: Subject to any disclaimer, the term of this patent is extended or adjusted under 35 U.S.C. 154(b) by 718 days.

This patent is subject to a terminal disclaimer.

(21) Appl. No.: 13/614,999

(22) Filed: Sep. 13, 2012

(65) Prior Publication Data
US 2013/0072771 A1    Mar. 21, 2013

(30) Foreign Application Priority Data
Sep. 21, 2011   (TW) .............................. 100133910 A (51) Int. Cl.
| | |
|---|---|
| A61B 5/1455 | (2006.01) |
| A61B 5/0205 | (2006.01) |
| G06F 3/033 | (2013.01) |
| A61B 5/00 | (2006.01) |
| A61B 5/024 | (2006.01) |
| G06F 3/03 | (2006.01) |
| G06F 3/042 | (2006.01) |
| G06F 3/0354 | (2013.01) |

(52) U.S. Cl.
CPC ........... *A61B 5/0205* (2013.01); *A61B 5/02433* (2013.01); *A61B 5/14551* (2013.01); *A61B 5/6897* (2013.01); *A61B 5/7207* (2013.01); *A61B 5/7214* (2013.01); *G06F 3/0304* (2013.01); *G06F 3/0354* (2013.01); *G06F 3/0425* (2013.01); *A61B 5/6826* (2013.01)

(58) Field of Classification Search
CPC ............... A61B 5/6886; A61B 5/6826; A61B 5/14552; A61B 5/7203; A61B 5/0205; A61B 5/7214; A61B 5/02433; A61B 5/14551; A61B 5/7207; A61B 5/02416
See application file for complete search history.

(56) References Cited

U.S. PATENT DOCUMENTS

| | | | |
|---|---|---|---|
| 5,983,120 A * | 11/1999 | Groner et al. ................. | 600/310 |
| 5,990,866 A * | 11/1999 | Yollin ............................ | 345/157 |
| 7,072,701 B2 | 7/2006 | Chen et al. | |
| 7,697,966 B2 * | 4/2010 | Monfre et al. ................ | 600/310 |
| 2009/0015558 A1 | 1/2009 | Hung | |
| 2010/0123655 A1 | 5/2010 | Lai | |
| 2010/0305418 A1* | 12/2010 | Deliwala ............ | A61B 5/14551 600/324 |

FOREIGN PATENT DOCUMENTS

CN        101853091 A       10/2010

* cited by examiner

*Primary Examiner* — Eric Winakur
(74) *Attorney, Agent, or Firm* — Hauptman Ham, LLP (57) ABSTRACT

There is provided an optical finger mouse including two light sources, an image sensor and a processing unit. The two light sources emit light of different wavelengths to illuminate a finger surface. The image sensor receives reflected light from the finger surface to generate a plurality of image frames. The processing unit detects a displacement and a contact status of the finger surface and a physiological characteristic of a user according to the plurality of image frames. There is further provided an electronic device and a physiological characteristic detection device.

20 Claims, 5 Drawing Sheets

OPTICAL FINGER MOUSE, ELECTRONIC DEVICE AND PHYSIOLOGICAL CHARACTERISTICS DETECTION DEVICE

CROSS REFERENCE TO RELATED APPLICATION

This application claims the priority benefit of Taiwan Patent Application Serial Number 100133910, filed on Sep. 21, 2011, the full disclosure of which is incorporated herein by reference.

BACKGROUND

1. Field of the Disclosure

This disclosure generally relates to a human interface device and, more particularly, to an optical finger mouse and a physiological characteristic detection device that may simultaneously detect a physiological characteristic of a user, a finger displacement and a finger contact status.

2. Description of the Related Art

As the optical finger mouse has a relatively small size, it is very suitable for being applied to portable electronic devices. An optical finger mouse can be used to detect an intensity variation of reflected light from a finger surface of a user so as to identify a finger contact status and a finger displacement with respect to a touch surface. However, with the development of industry, users spend more and more time on utilizing portable electronic devices that puts a lot of stress on their bodies. Therefore, if a portable electronic device also has the function of detecting physiological characteristics of a user and is able to give a warning when necessary, the overuse of the portable electronic devices can then be avoided.

Conventional pulse oximeters utilize a noninvasive method to monitor the blood oxygenation and the heart rate of a user. The conventional pulse oximeters generally emit a red light beam (wavelength of about 660 nm) and an infrared light beam (wavelength of about 910 nm) to penetrate a part of the human body and detects an intensity variation of the penetrating light based on the feature of the oxyhemoglobin and deoxyhemoglobin having different absorptivities in particular spectrum, e.g. referring to U.S. Pat. No. 7,072,701 and entitled "Method for spectrophotometric blood oxygenation monitoring". After the intensity variations of the penetrating light of the two wavelengths are detected, the blood oxygenation can be calculated according to equation (1):

$$\text{Oxygen saturation} = 100\% [\text{HbO}_2]/([\text{HbO}_2]+[\text{H}]) \quad (1)$$

wherein $[\text{HbO}_2]$ is oxyhemoglobin concentration; and [Hb] is deoxy-hemoglobin concentration.

Figure 1:
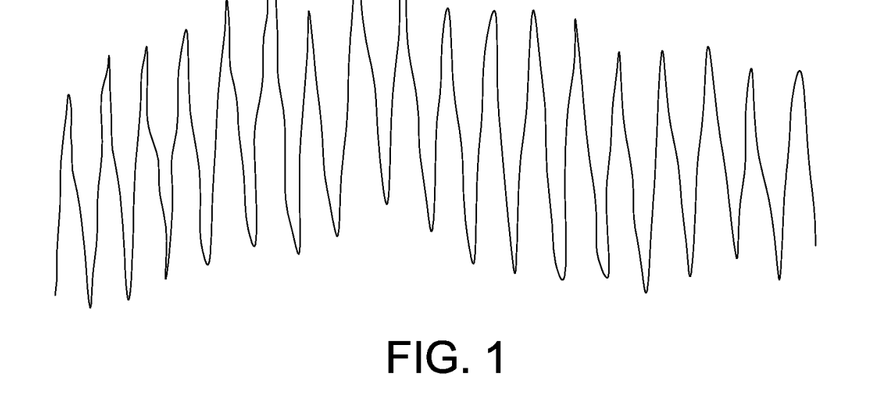
FIG. 1 shows a schematic diagram of an intensity variation of the penetrating light detected by a pulse oximeter.

Generally, the intensity variation of the penetrating light of the two wavelengths detected by a pulse oximeter is similar to FIG. 1. This is because blood vessels will expand and contract with heartbeats such that the blood volume that the light beams pass through will change to accordingly change the ratio of light energy being absorbed. Therefore, the absorptivity of blood of different light spectra can be calculated according to the intensity information changing continuously so as to calculate the physiology information, such as an oxyhemoglobin concentration and a deoxyhemoglobin concentration respectively. Finally, the blood oxygenation can be calculated according to equation (1).

However, as conventional pulse oximeters detect the intensity variation of the penetrating light, different intensity signals will be detected by detecting different parts of the human body. In addition, when the part of the human body being detected has a movement, a disturbed signal will be detected such that it is not possible to calculate correct physiological characteristics. Therefore, conventional pulse oximeters cannot be applied to portable electronic devices.

Accordingly, the present disclosure provides an optical finger mouse and a physiological characteristic detection method that may simultaneously detect physiological characteristics of a user, a finger displacement and a finger contact status, and can eliminate the signal noise caused by the movement.

SUMMARY

It is an object of the present disclosure to provide an optical finger mouse, an electronic device and a physiological characteristic detection device that may simultaneously calculate a finger displacement, a finger contact status and a physiological characteristic of a user by analyzing reflected light from a finger.

It is another object of the present disclosure to provide an optical finger mouse, an electronic device and a physiological characteristic detection device that may simultaneously detect a finger displacement, a finger contact status and a physiological characteristic of a user, and has a mechanism of eliminating the interference from ambient light sources.

It is another object of the present disclosure to provide an optical finger mouse, an electronic device and a physiological characteristic detection device that may simultaneously detect a finger displacement, a finger contact status and a physiological characteristic of a user, and has a denoising mechanism.

It is another object of the present disclosure to provide an optical finger mouse, an electronic device and a physiological characteristic detection device that may simultaneously detect a finger displacement, a finger contact status and a physiological characteristic of a user, and has a mechanism of regulating the system frequency.

It is another object of the present disclosure to provide an optical finger mouse, an electronic device and a physiological characteristic detection device that may simultaneously detect a finger displacement, a finger contact status and a physiological characteristic of a user, and may enter a sleep mode after idling for a predetermined time period.

It is another object of the present disclosure to provide an optical finger mouse, an electronic device and a physiological characteristic detection device that may simultaneously detect a finger displacement, a finger contact status and a physiological characteristic of a user, and the physiological characteristic may not be calculated or may be removed when the finger displacement is too large.

The present disclosure provides an optical finger mouse configured to detect a displacement and a physiological characteristic of a finger. The optical finger mouse includes a first light source, a second light source, a light control unit, an image sensor and a processing unit. The first light source emits light of a first wavelength to the finger. The second light source emits light of a second wavelength to the finger. The light control unit is configured to control an on-state and an off-state of the first light source and the second light source. The image sensor is configured to capture reflected light from the finger with a sampling frequency to generate a plurality of first image frames corresponding to the on-state of the first light source and a plurality of second image frames corresponding to the on-state of the second light source. The processing unit is configured to calculate the displacement and the physiological characteristic according to the first image frames and the second image frames.

The present disclosure further provides an electronic device configured to calculate and respond a displacement and a physiological characteristic of a finger. The electronic device includes an optical finger mouse, a controller and a response device. The optical finger mouse includes two light sources, a light control unit, an image sensor and a processing unit. The two light sources respectively emit light of different wavelengths to the finger. The light control unit is configured to control an on-state and an off-state of the two light sources. The image sensor is configured to capture reflected light from the finger with a sampling frequency to respectively generate a plurality of first image frames and second image frames corresponding to the on-state of the two light sources. The processing unit is configured to calculate and output the displacement and the physiological characteristic according to the first image frames and the second image frames. The controller receives the displacement and the physiological characteristic. The response device is controlled by the controller to respond at least one of the displacement and the physiological characteristic.

The present disclosure further provides a physiological characteristic detection device for calculating a physiological characteristic by means of detecting a part of the human body. The physiological characteristic detection device includes two light sources, a light control unit, an image sensor and a processing unit. The two light sources respectively emit light of different wavelengths to the part of the human body. The light control unit is configured to control an on-state and an off-state of the two light sources. The image sensor is configured to capture reflected light from the part of the human body with a sampling frequency to respectively generate a plurality of first image frames and a plurality of second image frames corresponding to the on-state of the two light sources. The processing unit is configured to divide each of the first image frames into at least two parts and calculate an average brightness of each part, and analyze the average brightness of the each part of the first image frames using independent component analysis to obtain a first intensity variation; to divide each of the second image frames into at least two parts and calculate an average brightness of each part, and analyze the average brightness of the each part of the second image frames using independent component analysis to obtain a second intensity variation; and to calculate the physiological characteristic according to the first intensity variation and the second intensity variation.

In the optical finger mouse, the electronic device and the physiological characteristic detection device of the present disclosure, the physiological characteristic includes a blood oxygenation and a heart rate. In the present disclosure, the movement informant and the physiology information are separated by means of independent component analysis (ICA) or blind source separation (BSS) so as to effectively eliminate the signal noise caused by the movement of the part of the human body being detected.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 2A:
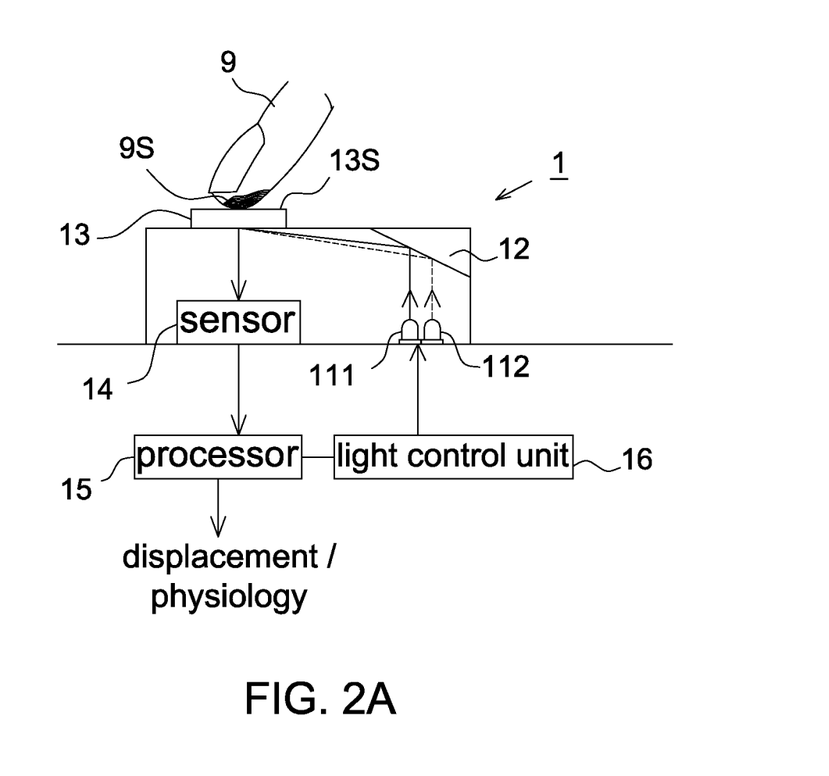
FIG. 2A shows a schematic diagram of the optical finger mouse according to an embodiment of the present disclosure.

Please refer to FIG. 2A, it shows a schematic diagram of the optical finger mouse 1 according to an embodiment of the present disclosure. The optical finger mouse 1 is configured to detect a displacement and a contact status of a finger 9 of a user with respect to the optical finger mouse 1, and to detect a physiological characteristic of the user, such as a blood oxygenation and a heart rate. Generally, the optical finger mouse 1 starts to calculate the displacement and the physiological characteristic when identifying that the contact status is a touch state (i.e. the finger 9 touches the optical finger mouse).

The optical finger mouse 1 includes two light sources 111 and 112, a light guide 12, a touch member 13, an image sensor 14, a processing unit 15 and a light control unit 16; in FIG. 2A, a spatial relationship between every component is only exemplary and not to limit the present disclosure. The two light sources 111 and 112 may be light emitting diodes or laser diodes to respectively emit light of different wavelengths. Preferably, said different wavelengths are two wavelengths used in conventional pulse oximeters, such as red light of wavelength about 660 nm and infrared light of wavelength about 905, 910 or 940 nm It is appreciated that the wavelengths mentioned herein are the center wavelength of corresponding spectrum.

The light guide 12 is configured to direct the light emitted by the light sources 111 and 112 to the touch member 13. The light guide 12 is not limited to a reflecting surface, and it may allow the light emitted by the light sources 111 and 112 to penetrate therein and transmit to the touch member 13. In other embodiments, if the light emitted from the light sources 111 and 112 can directly impinge on the touch member 13, the light guide 12 may not be implemented.

The touch member 13 has a touch surface 13S for the finger 9 to operate thereon, and the touch member 13 is preferably transparent to the light emitted by the light sources 111 and 112. When the finger 9 approaches or touches the touch surface 13S, the light emitted by the light sources 111 and 112 is reflected. It is appreciated that an area of the touch surface 13S may be larger or smaller than the finger surface 9S without any particular limitation.

The image sensor 14 receives, with a sampling parameter, reflected light from the touch member 13 (more specifically from the finger surface 9S) so as to generate a plurality of image frames, which may have a size of 16×16, wherein the sampling parameter may include an exposure time and image gain, but not limited thereto. It is appreciated that FIG. 2A may further include lens or lens set configured to direct the reflected light to the image sensor 14 so as to improve the sensing efficiency of the image sensor 14. The image sensor 14 is preferably an active matrix sensor, e.g. a CMOS image sensor, but it may be other devices for detecting images.

The processing unit 15 calculates a displacement and a contact status of the finger 9 with respect to the touch surface 13S and a physiological characteristic of a user according to the image frames from the image sensor 14. The displacement, contact status and physiological characteristic obtained by the processing unit 15 may be sent to an electronic device having a response device for displaying or corresponding control, wherein the response device may be a display device, a lamp device, a seven-segment display or a sound device. The electronic device may be a portable electronic device or a home appliance.

The light control unit 16 is coupled to the processing unit 15 and configured to control the ON/OFF (i.e. an on-state and an off-state) of the light sources 111 and 112 in correspondence with the image capturing of the image sensor 14, and details thereof will be illustrated hereinafter.

Figure 2B:
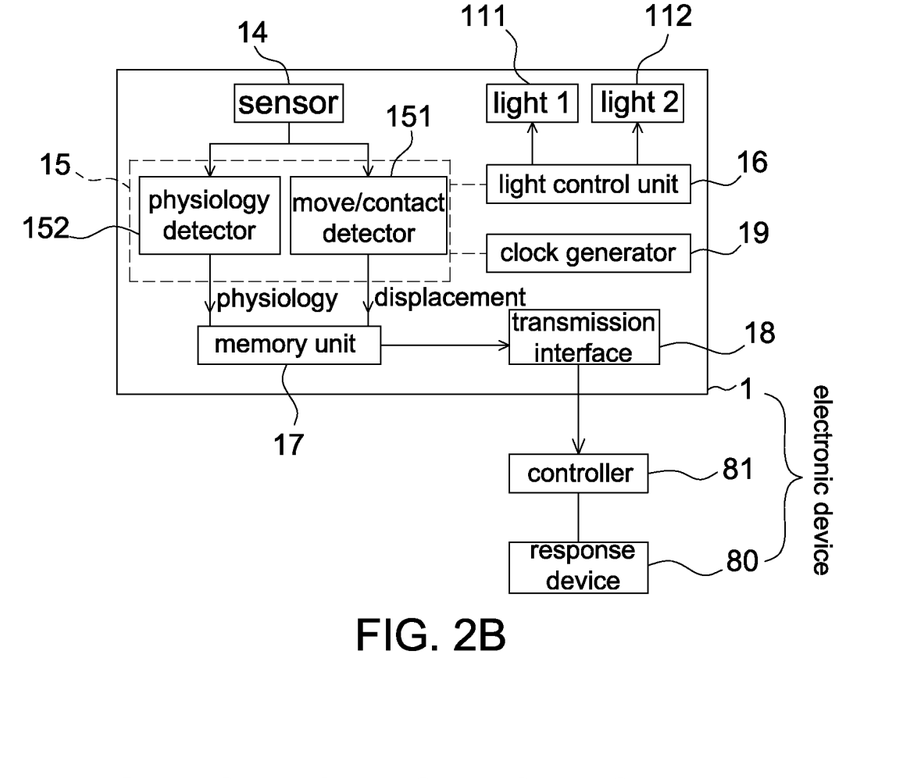
FIG. 2B shows a schematic block diagram of the optical finger mouse according to an embodiment of the present disclosure.

Please refer to FIGS. 2A and 2B, FIG. 2B shows a schematic block diagram of the optical finger mouse 1 according to the embodiment of the present disclosure. The optical finger mouse 1 includes a first light source 111, a second light source 112, the image sensor 14, the processing unit 15, the light control unit 16, a memory unit 17, a transmission interface 18 and a clock generator 19, wherein because the processing unit 15 is configured to perform multifunction calculation, the processing unit 15 may include a move/contact detection unit 151 configured to detect the displacement and contact status of the finger 9 with respect to the touch surface 13S and a physiology detection unit 152 configured to detect the physiological characteristic of the user. That is, the processing unit 15 may be a single element or be composed of two elements. The first light source 111 may emit red light of wavelength about 660 nm, and the second light source 112 may emit infrared light of wavelength about 905, 910 or 940 nm Broadly speaking, the first light source 111 and the second light source 112 respectively emit light of two wavelengths used in conventional pulse oximeters. Functions of the image sensor 14 and the light control unit 16 are illustrated above, and thus details thereof are not repeated herein. The memory unit 17 is configured to store the displacement, contact status, physiological characteristic obtained by the processing unit 15 and various parameters needed in calculation. The transmission interface 18 is configured to wired or wirelessly transmit the displacement, contact status and physiological characteristic stored in the memory unit 17 to a controller 81, wherein the technology of wired and wireless transmission is well known, and thus details thereof are not described herein. The controller 81 may be disposed inside or outside an electronic device having a response device 80 configured to control the electronic device to display and/or respond the received displacement, contact status and physiological characteristic through the response device 80. In one embodiment, the optical finger mouse 1, the controller 81 and response device 80 may compose an electronic device, e.g. a TV, a projection device or a computer system, wherein the controller 81 may be a remote controller, a mouse, a keyboard, an optical distance measuring device or other computer peripheral devices. In other words, the optical finger mouse 1, the controller 81 and the response device 80 may be coupled together wired or wirelessly so as to form a single device (e.g. a portable electronic device) or a plurality of devices physically separate from each other (e.g. a home appliance).

Therefore, the optical mouse finger 1 of the present disclosure may incorporate with an electronic device having a response device 80 such that when a user controls a cursor shown on the response device 80 or a software executed by the electronic device through the optical finger mouse 1, the response device 80 may simultaneously show the physiological characteristic of the user for reference. And when the physiological characteristic indicates that the user is in a fatigue state (e.g. according to a value of the physiological characteristic), a warning can be issued, wherein the method of showing the physiological characteristic and the warning may be performed by, for example, showing on a screen, representing by a lamp device or by sound controlled by a software. The clock generator 19 is configured to provide a system frequency.

In other embodiments, the optical finger mouse 1 may include two image sensors respectively configured to detect light of two different wavelengths, wherein an optical bandpass filter may be integrated with one or two of the image sensors in order to select the desired spectrum.

Sampling Mechanism

The optical finger mouse 1 of the present disclosure includes two light sources and may execute two functions simultaneously, wherein the detection function of the displacement and contact status does not need to use the image frames associated with specific wavelength, but the detection function of the physiological characteristic needs to be performed respectively corresponding to the image frames of different wavelengths. First, the sampling mechanism of the image frames in the present disclosure is illustrated.

Figure 3:
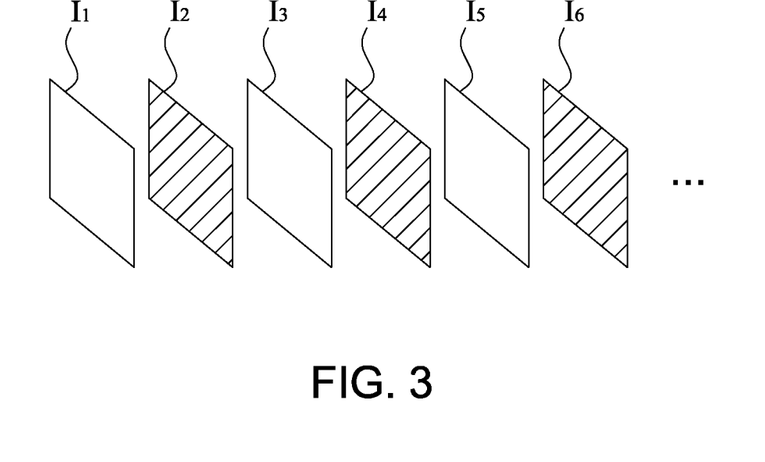
FIG. 3 shows a schematic diagram of the image frames captured by the image sensor of the optical finger mouse according to the embodiment of the present disclosure.

In one embodiment, the light control unit 16 controls the first light source 111 and the second light source 112 to light alternatively. The image sensor 14 captures image frames with a high and fixed sampling frequency (e.g. 3000 frames/sec) and synchronizing to the lighting (i.e. the on-state) of the first light source 111 or the second light source 112, and outputs a plurality of image frames $I_1$ to $I_6$ ..., as shown in FIG. 3, to the processing unit 15 (or simultaneously outputs the image frames to the move/contact detection unit 151 and the physiology detection unit 152), wherein the image frames $I_1$ to $I_6$ ... include first image frames $I_1, I_3, I_5$ ... corresponding to the on-state of the first light source 111 and second image frames $I_2, I_4, I_6$ ... corresponding to the on-state of the second light source 112.

The processing unit 15 (or the move/contact detection unit 151) may identify a contact status and calculate a displacement according to the first and second image frames $I_1$ to $I_6$ ..., e.g. identifying whether the finger 9 approaches or touches the touch surface 13S according to a comparison result of comparing a brightness value of the first and second image frames with at least one brightness threshold, wherein when the brightness value of the image frames is larger than or smaller than the brightness threshold, the system enters a touch state. After entering the touch state, the processing unit 15 may calculate the displacement according to the correlation between two first image frames, between one first image frame and one second image frame, or between two second image frames. It should be mentioned that although the method of identifying the contact status and calculating the displacement may use conventional methods, the identification and the calculation in the present disclosure need to use the image frames corresponding to the reflected light of two different wavelengths.

The processing unit 15 (or the physiology detection unit 152) may calculate an intensity variation of first image frame according to the first image frames $I_1, I_3, I_5 \ldots$, and calculates an intensity variation of second image frame according to the second image frames $I_2, I_4, I_6 \ldots$ (described later), and accordingly calculate the absorption ratio at two different spectra so as to obtain [HbO$_2$] and [Hb]. Finally, the blood oxygenation may be calculated according to equation (1), and the heart rate may also be calculated according to a comparison result of comparing the first image frames and/or the second image frames with at least one pulse threshold.

Figure 4:
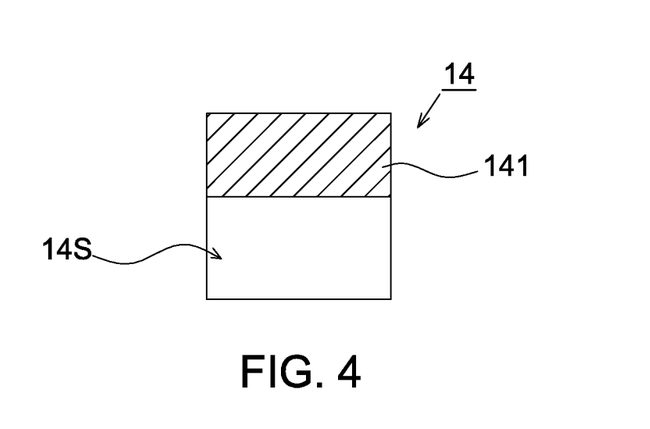
FIG. 4 shows a schematic diagram of the image sensor of the optical finger mouse according to the embodiment of the present disclosure, wherein an optical filter is disposed in front of a part of a sensing surface of the image sensor.

In another embodiment, the light control unit 16 controls the first light source 111 and the second light source 112 to light simultaneously and synchronizing to the image capturing of the image sensor 14; that is, the image sensor 14 may receive reflected light of two wavelengths simultaneously. Therefore, in this embodiment an optical filter 141 is further disposed in front of at least a part of a sensing surface 14S of the image sensor 14 as shown in FIG. 4, wherein the optical filter 141 may be an optical bandpass filter to allow the part of the sensing surface 14S behind the optical filter 141 to only receive the spectrum of the first light source 111 or the second light source 112, such that the processing unit 15 (or the move/contact detection unit 151 and the physiology detection unit 152) may distinguish the first image frame (i.e. the part of the image frame associated with the reflected light of the first light source 111) and the second image frame (i.e. the part of the image frame associated with the reflected light of the second light source 112). It is appreciated that in the present disclosure the position and the area of the optical filter 141 are not limited to those shown in FIG. 4.

In this manner, the processing unit 15 (or the move/contact detection unit 151) may also calculate a contact status and a displacement according to the first image frames and the second image frames $I_1$ to $I_6 \ldots$. The processing unit 15 (or the physiology detection unit 152) may also calculate the intensity variation of first image frame according to the first image frames $I_1, I_3, I_5 \ldots$, calculates the intensity variation of second image frame according to the second image frames $I_2, I_4, I_6 \ldots$, and calculates the blood oxygenation and the heart rate according to the two intensity variations.

It is appreciated that as the image sensor 14 may have different sensing efficiency of the light at different wavelengths, or the illumination brightness of the first light source 111 and the second light source 112 may be not exactly identical, the brightness of the image frames captured by the image sensor 14 may be previously adjusted (e.g. adjusting the sampling parameter, such as an exposure time and an image gain, of the image frames corresponding to different wavelengths) before shipment such that the image frames initially captured by the image sensor 14 may have substantially identical brightness so as to improve the identification accuracy.

In the present disclosure, the light control unit 14 is configured to control the on-states (lighting) and off-states (not lighting) of the first light source 111 and the second light source 112; the image sensor 14 captures reflected light from the finger 9 to generate a plurality of first image frames corresponding to the on-state of the first light source and a plurality of second image frames corresponding to the on-state of the second light source; and the processing unit 15 calculates the contact status, displacement and physiologically characteristic according to the first image frames and the second image frames.

Mechanism of Eliminating Ambient Light Interference

In FIG. 2A, as the touch member 13 and the finger 9 are light transmissive, the ambient light outside the optical finger mouse 1 can penetrate the finger 9 and the touch member 13 and be received by the image sensor 14 to degrade the image quality of the image frames captured thereby. In the present disclosure, the light control unit 16 may control the first light source 111 and the second light source 112 to turn off (i.e. the off-state) in predetermined time intervals.

Figure 5:
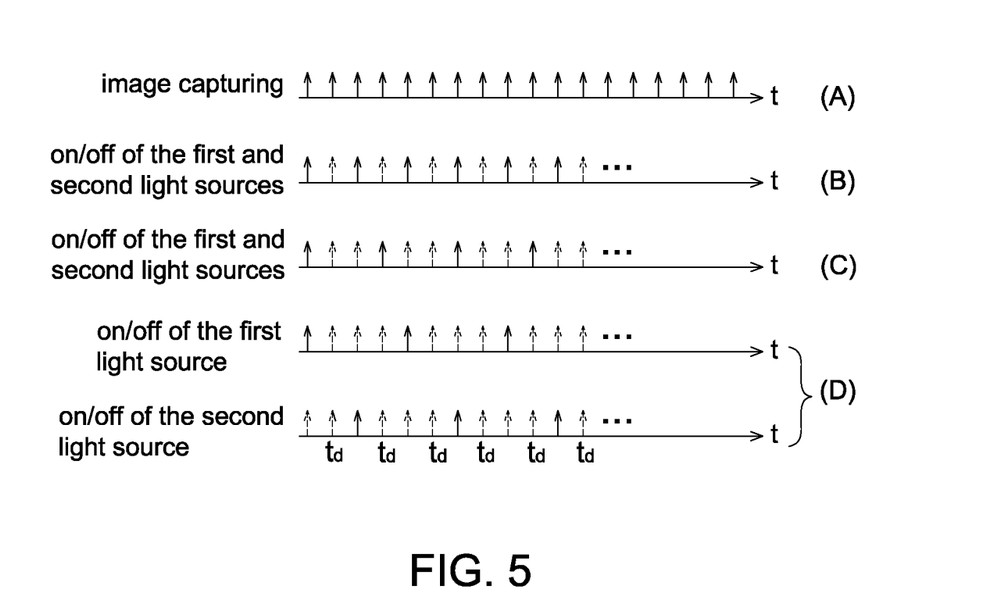
FIG. 5 shows a schematic diagram of the image capturing of the image sensor and the ON/OFF of the light source in the optical finger mouse according to the embodiment of the present disclosure.

For example please refer to FIG. 5, it shows a schematic diagram of the image capturing of the image sensor 14 and on-states and off-states of the first light source 111 and the second light source 112, wherein in FIGS. 5(B)-5(D) solid arrows denote the on-state of the light sources and dashed arrows denote the off-state of the light sources. FIG. 5(A) shows that the image sensor 14 captures image frames with a fixed sampling frequency. FIG. 5(B) shows that both the first light source 111 and the second light source 112 are alternatively turned on and turned off simultaneously, and thus the image sensor 14 may alternatively capture bright image frames (i.e. corresponding to the on-states of the light sources) and dark image frames (i.e. corresponding to the off-states of the light sources). FIG. 5(C) shows that the first light source 111 and the second light source 112 simultaneously turn on once after turning off two sampling periods (referring FIG. 5(A)), and this embodiment is generally for a lower displacement of the finger 9. As mentioned above, when the first light source 111 and the second light source 112 light simultaneously (FIGS. 5(B) and 5(C)), the image sensor 14 further includes an optical filter 141 for spatially distinguishing the image frame associated with different light sources such that one part of the image sensor 14 may sense the reflected light of the first light source 111 and the other part thereof may sense the reflected light of the second light source 112.

When the finger 9 touches or approaches the touch surface 13S, the bright image frames, which are associated with the on-states of the light sources, include components of (reflected light from finger +stray light +ambient light), and the dark image frames, which are associated with the off-states of the light sources, include only the component of (ambient light). Therefore, if a dark image frame is subtracted from a bright image frame, the interference from the ambient light can be effectively eliminated. The processing unit 15 may calculate the displacement, contact status and physiological characteristic according to differential images of the bright image frames and the dark image frames.

Please refer to FIG. 5(D), it shows an embodiment in which the first light source 111 and the second light source 112 are turned on alternatively. In this embodiment, in order to allow the image sensor 14 to be able to capture dark image frames, the light control unit 16 controls the first light source 111 and the second light source 112 to turn on alternatively every other image frame, e.g. the two light sources are both turned off at time $t_d$ in FIG. 5(D). Accordingly, the processing unit 15 may calculate a differential first image (i.e. bright first image frame—dark image frame) and a differential second image (i.e. bright second frame—dark image frame), and calculate the displacement, contact status and physiological characteristic according to the differential first and second images. As mentioned above, when the first light source 111 and the second light source 112 are turned on alternatively, the image sensor 14 temporally distinguishes the image frames associated with different light sources.

In the present disclosure, the light control unit 16 controls the first light source 111 and the second light source 112 to turn on simultaneously or alternatively to allow the image sensor 14 to be able to capture dark image frames when the light sources are turned off, and the interference from ambient light is eliminated by calculating a difference between bright and dark image frames. The on-states and off-states of each light source shown in FIG. 5 are only exemplary and not to limit the present disclosure.

Denoising Mechanism

As the image frames captured by the image senor 14 generally include noise which is randomly distributed in the image frames being captured.

Therefore, in the present disclosure it is able to calculate a sum of M image frames to increase the signal-to-noise ratio (SNR) thereby improving the calculation accuracy of the physiological characteristic. For example, it is able to calculate a sum of 10 image frames and every group of 10 image frames may have partially repeated image frames or totally different 10 image frames. It is appreciated that if the first light source 111 and the second light source 112 are turned on alternatively, the sum of M image frames in this embodiment may be a sum of M first image frames (e.g. $I_1+I_3+I_5+\ldots$ as shown in FIG. 3) and a sum of M second image frames (e.g. $I_2+I_4+I_6+\ldots$ as shown in FIG. 3) since two intensity variations need to be calculated respectively. However, if the first light source 111 and the second light source 112 are turned on simultaneously, the sum of M image frames in this embodiment is a sum of M successive image frames (e.g. $I_1+I_2+I_3+I_4+I_5+I_6+\ldots$ as shown in FIG. 3), and the two intensity variations may be distinguished by post-processing (i.e. spatially distinguishing). In addition, if the mechanism of eliminating interference from ambient light above is incorporated in this embodiment, the sum of M image frames of this embodiment is a sum of M differential images; that is, the process of eliminating interference from ambient light is performed first and then the denoising process is performed successively. In other embodiments, only one of the mechanism of eliminating interference from ambient light and the denoising mechanism is performed.

As mentioned above, the image sensor 14 may capture image frames with different sampling parameters, e.g. the image sensor 14 may have different absorptions of light at different wavelengths, and thus different sampling parameters, such as different exposure time and different image gain, may be used to have the first image frame and the second image frame have substantially identical brightness initially in order to correctly perform the post-processing on the image frames; that is, the sampling parameters associated with the first image frames and the second image frames may different. In the present disclosure, in order to eliminate the impact of different sampling parameters, every image frame, or a sum or an average of M image frames may be normalized by the sampling parameter, e.g. (a sum of M image frames/sampling parameter) or (an average of M image frames/sampling parameter), wherein M is a positive integer.

Calculating Physiological Characteristic

Corresponding to the on-states of different light sources, the image frames captured by the image sensor 14 may contain physiology information and movement information at the same time. Therefore, in the present disclosure the processing unit 15 (or the physiology detection unit 152) has to separate two types of information at first and then is able to calculate the physiological characteristic correctly. In the present disclosure, the processing unit 15 may separate the two types of information according to, for example, independent component analysis (ICA) or blind source separation (BSS).

Figure 6:
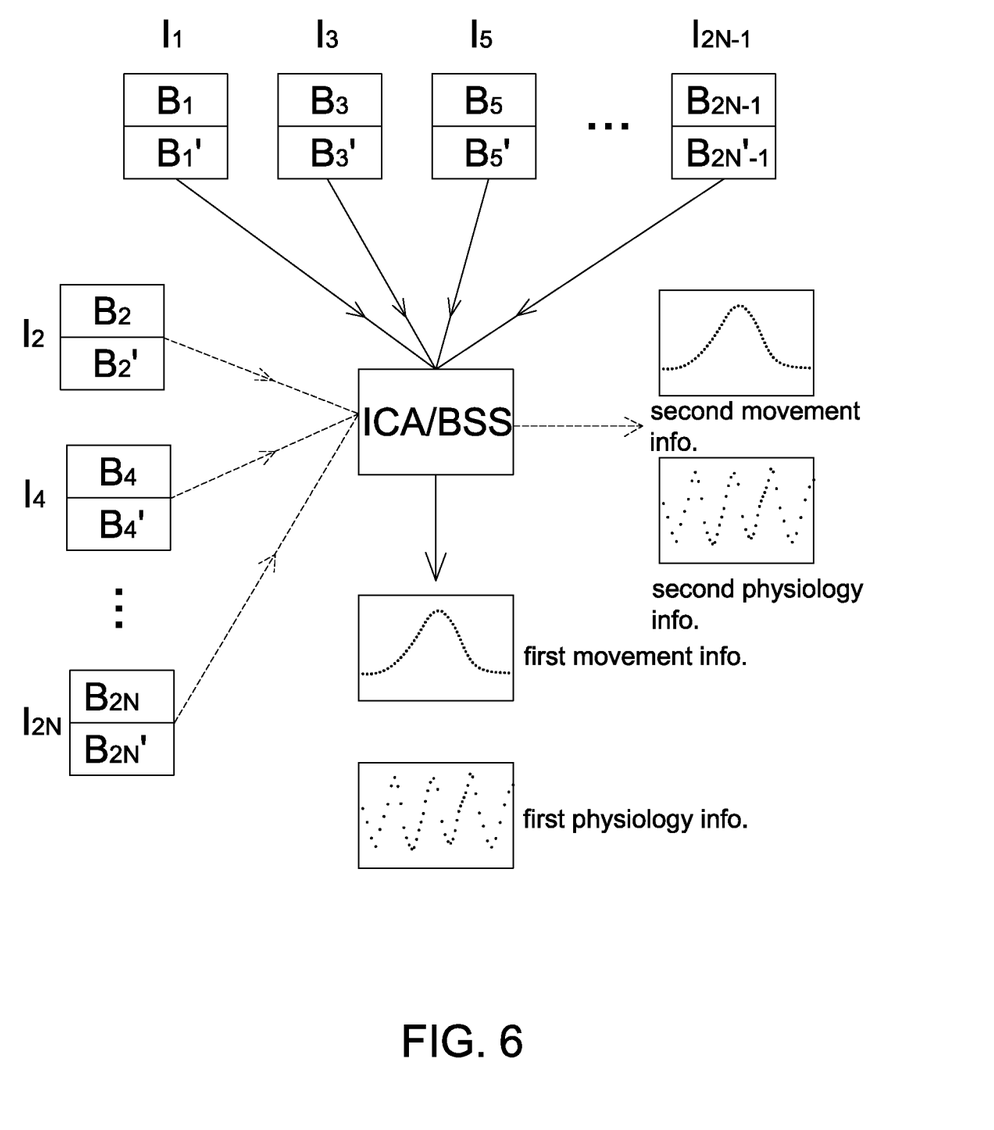
FIG. 6 shows a schematic diagram of the separation of the movement information and the physiology information by the processing unit of the optical finger mouse according to the embodiment of the present disclosure.

Please refer to FIGS. 3 and 6, first taking the first image frames $I_1, I_3, I_5 \ldots$ shown in FIG. 3 as an example, each of the first image frames (e.g. original first image frames or the first image frames processed by the mechanism of eliminating interference from ambient light and/or normalization) or each of the sum of a plurality of first image frames (e.g. a sum of M original first image frames or a sum of M first image frames processed by the mechanism of eliminating interference from ambient light and/or normalization) is divided into at least two parts and an average brightness of each part is calculated, e.g. the image frame $I_1$ is divided into an upper and a lower part respectively having an average brightness $B_1$ and $B_1'$; the image frame $I_3$ is divided into an upper and a lower part respectively having an average brightness $B_3$ and $B_3'$; ...; the image frame $I_{2N-1}$ is divided into an upper and a lower part respectively having an average brightness $B_{2N-1}$ and $B_{2N-1}'$, wherein the image frames may be divided into more than two parts in other embodiments. Next, a first movement informant and a first physiology information is separated from the divided image frames according to independent component analysis (ICA) or blind source separation (BSS) method as shown in FIG. 6, and both information is shown as a curve of intensity variation. In the present disclosure the movement information is abandoned and the physiological characteristic is calculated only according to the physiology information. It is appreciated that as the sampling frequency of the image sensor 14 is much higher than the heart rate, the separated physiology information is shown as a curve of the intensity variation corresponding to the pulse beating (similar to FIG. 1), and the separated movement information is not limited to that shown in FIG. 6. In addition, the two parts divided from the image frames are not necessary to be the upper and lower parts of the image frames. In addition, as it is necessary to respectively calculate the physiology information of two different wavelengths, the aforementioned separation process is performed respectively on the first image frames $I_1, I_3, I_5 \ldots$ (i.e. corresponding to the on-state of the first light source) and the second image frames $I_2, I_4, I_6 \ldots$ (i.e. corresponding to the on-state of the second light source). It should be mentioned that, if the information separation is performed on the sum or average of the image frames, each of the $I_1$ to $I_{2N-1}$ and $I_2$ to $I_{2N}$ shown in FIG. 6 represents a sum or an average of M image frames.

It should be emphasized that the displacement and the contact status of the finger 9 are calculated by the processing unit 15 (or the move/contact detection unit 151) directly according to the original first image frames and second image frames without using the separated movement information. The ICA and BSS methods are mainly configured to separate combined signals so as to eliminate the signal noise caused by movement.

In the present disclosure, the processing unit 15 further calculates a heart rate according to a comparison result of comparing at least one pulse threshold with the first intensity variation (i.e. the first physiology information) and/or the second intensity variation (i.e. the second physiology information).

Mechanism of Regulating System Frequency

In order to reduce the system cost, the clock generator 19 may use a RC oscillator circuit. Although the RC oscillator circuit has a lower cost, it also has a lower precision as its oscillating frequency can change with the manufacturing process and operating temperature. However, the crystal oscillator may also be utilized in other embodiments. In calculating the physiological characteristic, a precise system frequency is necessary (e.g. in calculating heart rate). Therefore, preferably a reference to regulate the oscillating frequency of the clock generator 19 of the optical finger mouse 1 may be constructed before shipment; for example, an external light source having a precise lighting frequency may be attached to the touch surface 13S of the touch member 13 to allow the image sensor 14 to detect the intensity variation of the external light source; then, a difference between the oscillating frequency of the clock generator 19 under different operating temperatures and the precise lighting frequency may be recorded previously to be served as a system frequency calibration parameter and pre-stored in the memory unit 17. And the system frequency can be precisely adjusted based on the system frequency calibration parameter when necessary.

Sleep Mode

The optical finger mouse 1 of the present disclosure may enter a sleep mode after idling for a predetermined time period. For example, when the processing unit 15 identifies that a finger 9 does not approach or touch the touch surface 13S within a predetermined time period, it enters the sleep mode.

Mechanism of Removing Physiological Characteristic

The processing unit 15 of the optical finger mouse 1 of the present disclosure may calculate the displacement and the physiological characteristic simultaneously, but accurate physiological characteristic can only be obtained when the displacement is relatively low. Therefore, in the present disclosure the processing unit 15 may previously identify whether the displacement is larger than a predetermined value (i.e. a displacement threshold). When the displacement is larger than the predetermined value, the image frames captured by the image sensor 14 are only used to calculate the displacement or to identify the contact status but not to calculate the physiological characteristic; or even though the physiological characteristic is calculated, the physiological characteristic is directly removed from the memory unit 17 without being transmitted via the transmission interface 18.

Figure 7:
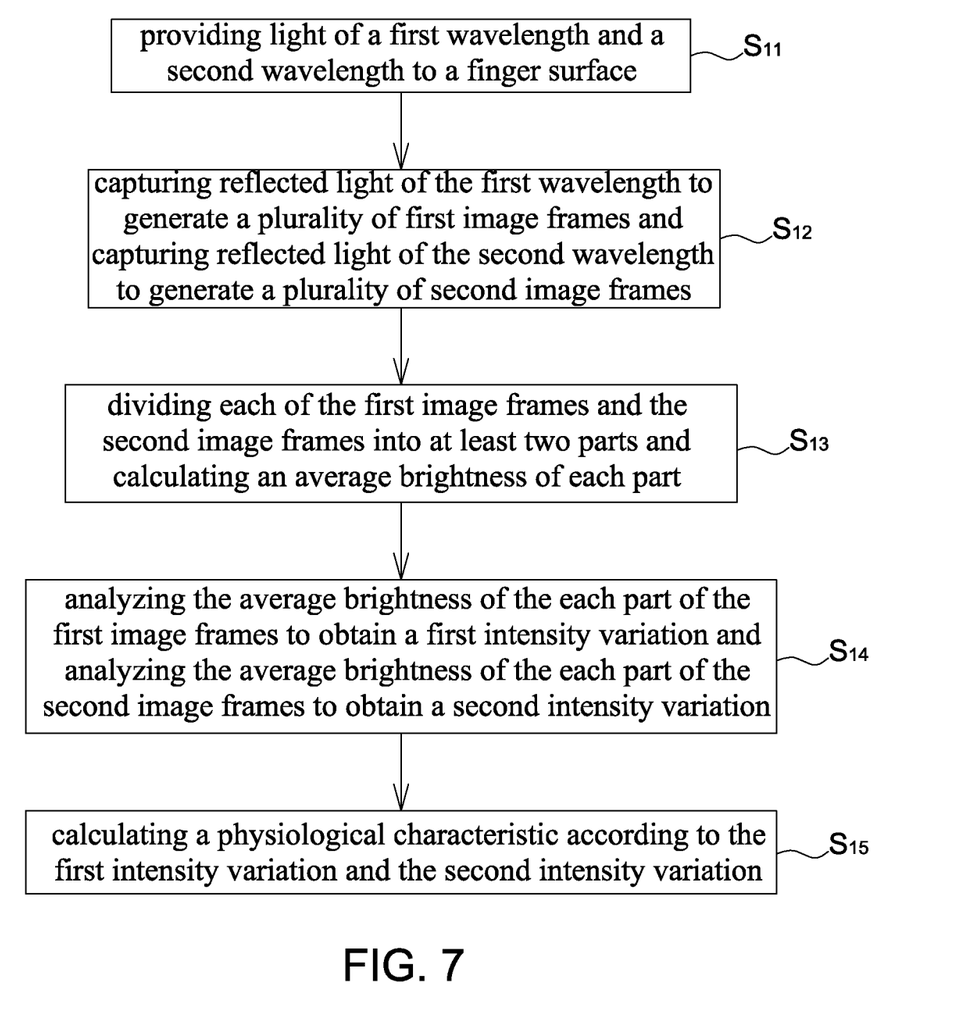
FIG. 7 shows a flow chart of the physiological characteristic detection method according to an embodiment of the present disclosure.

The present disclosure further provides a physiological characteristic detection method including the steps of: providing light of a first wavelength and a second wavelength to a finger surface (Step $S_{11}$); capturing reflected light of the first wavelength to generate a plurality of first image frames and capturing reflected light of the second wavelength to generate a plurality of second image frames (Step $S_{12}$); dividing each of the first image frames and the second image frames into at least two parts and calculating an average brightness of each part (Step $S_{13}$); using independent component analysis or blind source separation to analyze the average brightness of the each part of the first image frames to obtain a first intensity variation and to analyze the average brightness of the each part of the second image frames to obtain a second intensity variation (Step $S_{14}$); and calculating a physiological characteristic according to the first intensity variation and the second intensity variation (Step $S_{15}$). The physiological characteristic detection method of this embodiment is suitable for an electronic device having an optical finger mouse and preferably including a response device. Details of every step of this embodiment have been illustrated above and thus are not repeated herein.

In addition, the physiological characteristic detection method of the present disclosure is not only can be applied to an optical finger mouse, it may also be applied to a physiological characteristic detection device to replace conventional pulse oximeters configured to calculate physiological characteristics through detecting the skin surface of a part of the human body. In this embodiment, only the finger 9 used in aforementioned embodiments needs to be replaced by another part of the human body, in addition to not calculating the displacement, the method of calculating the physiological characteristics is similar, and thus details thereof are not repeated herein. That is, said physiological characteristic detection device may also have the mechanisms of denoising, eliminating interference from ambient light, entering sleep mode and regulating the system frequency. Said another part of the human body may be the part of the human body to be detected in conventional pulse oximeters.

As mentioned above, a conventional optical finger mouse can not detect physiological characteristics of a user and a method of calculating the blood oxygenation for pulse oximeters can not be applied to an optical finger mouse since the method can not detect a moving object. Therefore, the present disclosure further provides an optical finger mouse (FIGS. 2A and 2B) that can detect the finger displacement and the physiological characteristics of a user simultaneously, and can effectively eliminate the signal noise caused by movement and the interference from ambient light source, and further has the mechanisms of regulating the system frequency, entering sleep mode and removing invalid physiology information.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. An optical finger mouse configured to detect a displacement of a finger of a user and a physiological characteristic of the user, the optical finger mouse comprising:
    a first light source configured to emit light of a first wavelength to the finger;
    a second light source configured to emit light of a second wavelength to the finger;
    a light control unit configured to control an on-state and an off-state of the first light source and the second light source;
    an image sensor configured to capture reflected light from the finger with a sampling frequency to generate a plurality of first image frames corresponding to the on-state of the first light source and a plurality of second image frames corresponding to the on-state of the second light source; and
    a processing unit configured to calculate both of the displacement of the finger for controlling a cursor and the physiological characteristic according to the first image frames and the second image frames captured by the image sensor,
    wherein in calculating the physiological characteristic, the processing unit is configured to
        divide each of the first image frames into at least two parts and calculate an average brightness of each part,
        analyze the average brightness of the each part of the first image frames to obtain a first intensity variation,
        divide each of the second image frames into at least two parts and calculate an average brightness of each part,
        analyze the average brightness of the each part of the second image frames to obtain a second intensity variation, and
        calculate the physiological characteristic according to the first intensity variation and the second intensity variation.

2. The optical finger mouse as claimed in claim 1, wherein the physiological characteristic comprises a blood oxygenation and a heart rate.

3. The optical finger mouse as claimed in claim 1, wherein the processing unit is further configured to calculate a heart rate according to a comparison of at least one pulse threshold with at least one of the first intensity variation and the second intensity variation.

4. The optical finger mouse as claimed in claim 1, wherein the processing unit is further configured to calculate a sum of M image frames for denoising, and normalize the sum or an average of the M image frames with a sampling parameter, wherein M is a positive integer.

5. The optical finger mouse as claimed in claim 1, wherein
   the light control unit is configured to enable the off-state of the first light source and the second light source in predetermined time intervals such that the image sensor captures a plurality of bright first image frames, a plurality of bright second image frames and a plurality of dark image frames; and
   the processing unit is configured to calculate the displacement and the physiological characteristic according to a difference between the bright first image frames and the dark image frames and according to a difference between the bright second image frames and the dark image frames.

6. The optical finger mouse as claimed in claim 1, wherein the optical finger mouse is configured to enter a sleep mode after idling for a predetermined time period.

7. The optical finger mouse as claimed in claim 1, wherein the processing unit is configured to not calculate or is configured to ignore the physiological characteristic when the displacement is larger than a predetermined value.

8. The optical finger mouse as claimed in claim 1, further comprising a memory unit configured to store a system frequency calibration parameter.

9. The optical finger mouse as claimed in claim 1, wherein the processing unit is further configured to compare a brightness value of the first image frames and the second image frames with a brightness threshold to identify a contact status of the finger with the optical finger mouse.

10. The optical finger mouse as claimed in claim 9, wherein the displacement and the physiological characteristic are calculated when the contact status is identified as a touch state.

11. The optical finger mouse as claimed in claim 1, wherein the processing unit is configured to calculate the displacement according to two of the first image frames, one of the first image frames and one of the second image frames, and two of the second image frames.

12. The optical finger mouse as claimed in claim 1, wherein
   the light control unit is configured to alternatively enable the on-state of the first light source and the second light source such that the image sensor receives the reflected light associated with the first light source and the second light source alternatively; or
   the light control unit is configured to simultaneously enable the on-state of the first light source and the second light source such that the image sensor receives the reflected light associated with the first light source and the second light source simultaneously, and the image sensor comprises an optical filter covering at least a part of a sensing surface thereof.

13. An electronic device configured to calculate and respond to a displacement of a finger of a user and a physiological characteristic of the user, the electronic device comprising:
   an optical finger mouse comprising:
      two light sources respectively configured to emit light of different wavelengths to the finger;
      a light control unit configured to control an on-state and an off-state of the two light sources;
      an image sensor configured to capture reflected light from the finger with a sampling frequency to generate a plurality of first image frames and a plurality of second image frames respectively corresponding to the on-state of the two light sources; and
      a processing unit configured to calculate both of the displacement of the finger for controlling a cursor and the physiological characteristic according to the first image frames and the second image frames captured by the image sensor, and output the displacement and the physiological characteristic,
      wherein in calculating the physiological characteristic, the processing unit is configured to
         divide each of the first image frames into at least two parts and calculate an average brightness of each part,
         analyze the average brightness of the each part of the first image frames to obtain a first intensity variation,
         divide each of the second image frames into at least two parts and calculate an average brightness of each part,
         analyze the average brightness of the each part of the second image frames to obtain a second intensity variation, and
         calculate the physiological characteristic according to the first intensity variation and the second intensity variation;
   a controller configured to receive the displacement and the physiological characteristic; and
   a response device controlled by the controller to respond to at least one of the displacement and the physiological characteristic.

14. The electronic device as claimed in claim 13, wherein
   the response device is a display device, a lamp device, a seven-segment display or a sound device; and
   the controller is a remote controller, a mouse, a keyboard or an optical distance measuring device.

15. The electronic device as claimed in claim 13, wherein the physiological characteristic comprises a blood oxygenation and a heart rate.

16. The electronic device as claimed in claim 13, wherein the processing unit is further configured to calculate a heart rate according to a comparison of at least one pulse threshold with at least one of the first intensity variation and the second intensity variation.

17. The electronic device as claimed in claim 13, wherein the processing unit is further configured to compare a brightness value of the first image frames and the second image frames with a brightness threshold to identify a contact status of the finger with the optical finger mouse.

18. The electronic device as claimed in claim 17, wherein the displacement and the physiological characteristic are calculated when the contact status is identified as a touch state.

19. A physiological characteristic detection device configured to calculate a physiological characteristic by detecting a part of a human body, the physiological characteristic detection device comprising:
   two light sources configured to respectively emit light of different wavelengths to the part of the human body;
   a light control unit configured to control an on-state and an off-state of the two light sources;
   an image sensor configured to capture reflected light from the part of the human body with a sampling frequency to generate a plurality of first image frames and a plurality of second image frames respectively corresponding to the on-state of the two light sources; and a processing unit configured to
- divide each of the first image frames into at least two parts and calculate an average brightness of each part,
- analyze the average brightness of the each part of the first image frames using independent component analysis to obtain a first intensity variation,
- divide each of the second image frames into at least two parts and calculate an average brightness of each part,
- analyze the average brightness of the each part of the second image frames using independent component analysis to obtain a second intensity variation, and
- calculate the physiological characteristic according to the first intensity variation and the second intensity variation.

20. The physiological characteristic detection device as claimed in claim 19, wherein the physiological characteristic comprises a blood oxygenation and a heart rate.

* * * * *